United States Patent
Werblud

(10) Patent No.: US 6,378,648 B1
(45) Date of Patent: Apr. 30, 2002

(54) DIAPHRAGM ASSEMBLY FOR STETHOSCOPE CHEST PIECE

(76) Inventor: Marc S. Werblud, 9426 NE. 139th St., Kirkland, WA (US) 98034

( * ) Notice: Subject to any disclaimer, the term of this patent is extended or adjusted under 35 U.S.C. 154(b) by 0 days.

(21) Appl. No.: 09/518,945

(22) Filed: Mar. 6, 2000

(51) Int. Cl.7 .................................................. A61B 7/02
(52) U.S. Cl. ...................................... 181/131; 181/132
(58) Field of Search ................................ 181/131, 132, 181/134, 135, 136, 137

(56) References Cited

U.S. PATENT DOCUMENTS

| | | | | |
|---|---|---|---|---|
| 3,910,376 A | * | 10/1975 | Azneer | 181/131 |
| 4,239,089 A | * | 12/1980 | Nelson | 181/131 |
| 4,475,619 A | * | 10/1984 | Packard | 181/137 |
| 4,770,270 A | * | 9/1988 | Grimm | 181/137 |
| 4,776,426 A | * | 10/1988 | Kazama | 181/131 |
| 4,867,268 A | * | 9/1989 | Ulert | 181/137 |
| 5,269,314 A | * | 12/1993 | Kendall et al. | 128/715 |
| 5,365,023 A | * | 11/1994 | Lawton | 181/131 |

* cited by examiner

Primary Examiner—Robert E. Nappi
Assistant Examiner—Kim Lockett
(74) Attorney, Agent, or Firm—Robert W. Jenny

(57) ABSTRACT

The diaphragm assembly includes a diaphragm adhesively attached to a rim. The rim has a C-shaped cross section with the C-shape facing inward and a membrane extending radially inward from one of the radial portions of the C-shaped portion. The diaphragm is attached to the membrane. The thickness of the membrane is about two tenths of the thickness of the section of the C-shaped portion. The groove formed by the C-shape engages a rib on a stethoscope chest piece to install the diaphragm assembly.

1 Claim, 1 Drawing Sheet

DIAPHRAGM ASSEMBLY FOR STETHOSCOPE CHEST PIECE

BACKGROUND OF THE INVENTION

1. Field

The subject invention is in the field of devices used to produce acoustic energy, in particular diaphragms which, when activated, produce acoustic energy. For purposes of this disclosure, acoustic energy is the energy of waves in atmosphere which produce sound when perceived by ears of humans and animals and by electronic equipment such as microphones and associated amplifiers, speakers, etc. In particular, the subject invention is in the field of diaphragms for use on the chest pieces of stethoscopes. When a chest piece is placed on the surface of a human body the motions of the surface activate the diaphragm to generate acoustic energy which is transmitted to the user's ears and perceived as sounds having specific, significant characteristics.

Such diaphragms operate in two modes. In one the rim or effective rims of the diaphragm is/are fixed and the functional characteristics of the diaphragm are determined by its physical characteristics. In a second mode the diaphragm is supported by flexible structure which is called a surround. In this mode the functional characteristics of the diaphragm are determined primarily by the physical characteristics of the surround. The subject invention is in the specific field of chest piece diaphragms operable in this second mode.

2. Prior Art

Prior art stethoscope diaphragms usable in the second mode are known to comprise a diaphragm or diaphragm subassembly and some type of retainer for attaching the diaphragm or diaphragm subassembly to the stethoscope chest piece. Examples of this prior art can be found in U.S. Patents 4,440,258 and 5,945,640. It is well known in the trade that (1) for these diaphragms to function as intended they must be correctly installed, (2) that it requires considerable experience and skill to correctly install the diaphragms, and (3) they can easily be installed with hard to detect imperfection, resulting in poor performance.

Therefore, the primary objective of the subject invention is to provide a stethoscope diaphragm assembly which operates in the second mode as defined above, and can be easily correctly installed with incorrect installation clearly obvious.

SUMMARY OF THE INVENTION

The subject invention is a diaphragm assembly for a stethoscope chest piece. The assembly comprises a diaphragm and a surround which are permanently attached to each other. The diaphragm is a plastic disc. The surround is elastomeric and a body of revolution having a rim portion which is relatively stiff because of its thickness and a membrane portion extending radially inward from the rim portion, the membrane portion being relatively flexible because it is relatively thin. The diameter of the diaphragm is smaller than the inside diameter of the rim portion so that when the diaphragm is adhesively concentrically attached to the membrane portion of the surround there is a circular portion of the membrane portion between the diaphragm and the rim portion. The rim portion is grooved on its inside diameter and the groove engages a ridge on the chest piece to hold the diaphragm assembly in place. The circular portion of the membrane allows the diaphragm to translate on its centerline to operate in the second mode as noted above.

The invention is described in more detail below with reference to the attached drawings.

DETAILED DESCRIPTION OF THE INVENTION

Figure 1:
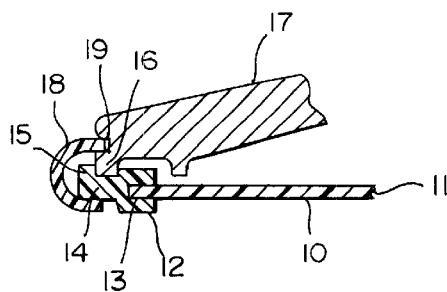
FIG. 1 is a schematic section of the edge portion of a first prior art diaphragm assembly installed on a chest piece.

The subject invention is a diaphragm assembly for stethoscope chest pieces. FIG. 1 is a schematic section of the rim portion of a first prior art diaphragm installed on a chest piece. Diaphragm assembly 10 comprises plastic diaphragm 11 and elastomeric rim 12 adhesively attached to each other. The rim comprises U-shaped portion 13, ring portion 14 and flange 15. Flange 15 and ring portion 14 engage rib 16 on chest piece body 17. Retainer ring 18 retains the assembly diaphragm in place by engagement in groove 19 of the body and ring portion 14. There are three pieces involved in the diaphragm assembly and its attachment to the body and one piece is a loose piece.

Figure 2:
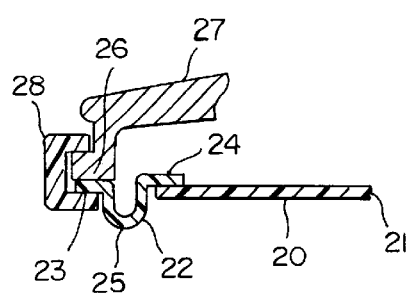
FIG. 2 is a schematic section of the edge portion of a second prior art assembly installed on a chest piece.

FIG. 2 is a schematic section of the rim portion of a second prior art diaphragm assembly installed on a chest piece. The diaphragm assembly 20 comprises plastic diaphragm 21 and elastomeric rim 22. Rim 22 comprises ring portions 23 and 24 interconnected by channel portion 25. Ring portion 24 is adhesively attached to the diaphragm and ring portion 23 contacts flange 26 on chest piece body 27 and the diaphragm assembly is attached to the body by retainer ring 28 which has a C-shaped cross section. In this prior art also there are three pieces involved in the diaphragm assembly and its attachment to the body and one piece is a loose piece. The diaphragm assemblies of FIGS. 1 and 2 may be incorrectly installed with the fault hidden from view by the retainer ring.

Figure 3:
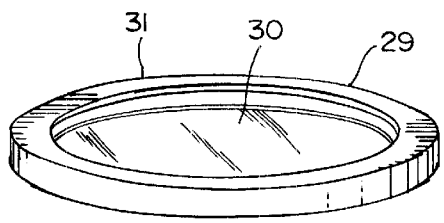
FIG. 3 is a general view of the subject diaphragm assembly.

FIG. 3 is a general view of the subject diaphragm assembly 29. It comprises plastic diaphragm 30 and rim 31 adhesively attached to each other.

Figure 4:
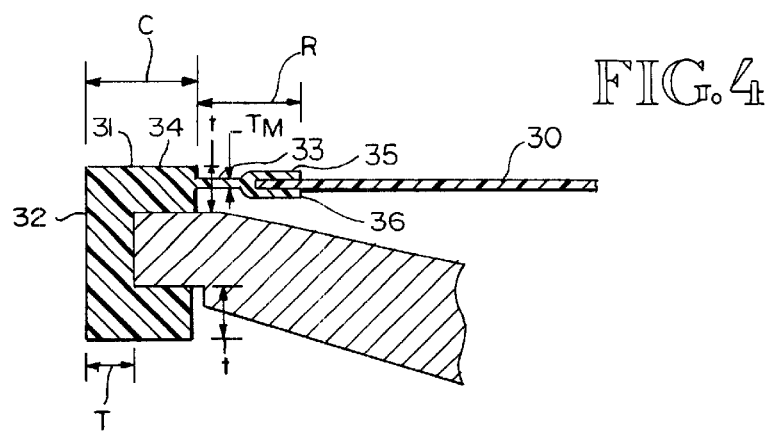
FIG. 4 is a schematic section of the edge portion of the subject diaphragm installation on a chest piece.
Figure 4A:
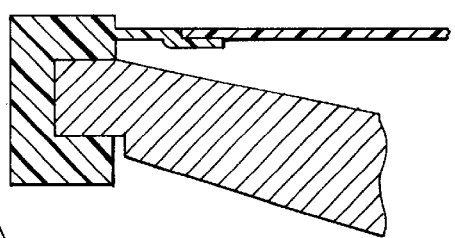
FIG. 4A illustrates an alternate membrane configuration. Also, the membrane could be flat.

FIG. 4 is a schematic section of the edge portion of assembly 29 installed on a chest piece 30. Rim 31 comprises a ring portion 32 having a C-shaped cross section. Thickness T of portion 32 is in a range of 0.4 to 0.6 of circumferential dimension C of the ring portion, with 0.5 preferred. Thicknesses t of the ring portion may be equal, with t essentially equal to T. Rim 31 also comprises membrane 33 which extends radially inward from radial portion 34 of ring portion 32. Membrane 33 is bifurcated, producing bifurcations 35 and 36 and the diaphragm 30 is adhesively installed between the bifurcations. Radial dimension r of the membrane is in a range of 0.5 to 1.5 times C with 1.5 preferred. Thickness Tm is in a range of 0.1 to 0.3 of t with 0.2 preferred. In other words, the thickness dimensions of the ring portion are 3 to 10 times those of the membrane with 7 preferred. The membrane may not be bifurcated but instead stepped as shown in FIG. 4A. The step serves to center the diaphragm on the membrane during assembly. The characteristics of the membrane allow the diaphragm to translate parallel to itself. The diaphragm assembly and its attachment to the past comprise two parts and no part is loose.

It is considered to be understood from this description that the subject invention meets its objectives. It provides a stethoscope diaphragm assembly which operates in the second mode as defined above and can be easily correctly installed. Incorrect installation is clearly obvious because none of the membrane support material is hidden from view.

It is also considered to be understood that while one embodiment of the subject invention is disclosed herein, other embodiments and modifications of the one disclosed are possible within the scope of the invention which is limited only by the attached claims.

What is claimed is:

1. A stethoscope diaphragm assembly comprising:

a diaphragm and a rim, said diaphragm being adhesively attached to said rim, said rim comprising (1) a ring portion having a C-shaped cross section shape and (2) a membrane portion extending radially inward from said ring portion, said diaphragm being attached to said membrane, said ring portion having first thickness dimensions and said membrane having second thickness dimensions and said first thickness dimensions are in a range of 3 to 10 times said second thickness dimensions.

* * * * *